United States Patent
Dennerlein et al.

(10) Patent No.: US 9,779,498 B2
(45) Date of Patent: Oct. 3, 2017

(54) DEVICE AND METHOD FOR ASSESSING X-RAY IMAGES

(71) Applicants: Frank Dennerlein, Eckental (DE); Oliver Schütz, Erlangen (DE)

(72) Inventors: Frank Dennerlein, Eckental (DE); Oliver Schütz, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 70 days.

(21) Appl. No.: 14/855,893

(22) Filed: Sep. 16, 2015

(65) Prior Publication Data
US 2016/0086329 A1 Mar. 24, 2016

(30) Foreign Application Priority Data
Sep. 19, 2014 (DE) .................. 10 2014 218 893

(51) Int. Cl.
*G06T 7/00* (2017.01)
*A61B 6/02* (2006.01)
(Continued)

(52) U.S. Cl.
CPC ............ *G06T 7/0012* (2013.01); *A61B 6/025* (2013.01); *A61B 6/4452* (2013.01); *A61B 6/5211* (2013.01); *A61B 6/5258* (2013.01); *G06K 9/4604* (2013.01); *G06T 7/20* (2013.01); *G06T 11/008* (2013.01); *G06T 15/00* (2013.01); *G06T 19/00* (2013.01); *A61B 6/027* (2013.01);
(Continued)

(58) Field of Classification Search
CPC ...... G06K 9/4604; A61B 6/025; A61B 6/027; A61B 6/4452; A61B 6/5205; A61B 6/5211; A61B 6/5258; G06T 7/0012; G06T 7/20; G06T 11/008; G06T 15/00; G06T 19/00; G06T 2207/10116; G06T 2211/436
See application file for complete search history.

(56) References Cited

U.S. PATENT DOCUMENTS 7,822,255 B2 10/2010 Schutz
8,619,944 B2 12/2013 Dennerlein et al.
(Continued)

FOREIGN PATENT DOCUMENTS

DE 102005043051 A1 3/2007
DE 102009020400 A1 11/2010
(Continued)

OTHER PUBLICATIONS

Noo et al., "Image reconstruction from fan-beam projections on less than a short scan", Phys. Med. Biol. 47 (2002) 2525-2546.*
(Continued)

*Primary Examiner* — Katrina Fujita
(74) *Attorney, Agent, or Firm* — Lempia Summerfield Katz LLC

(57) ABSTRACT

In the present embodiments, a statement related to an image point or an image region in a reconstructed x-ray image is made in relation to the reliability of the reconstructed grayscale value for the image points of a 2D/3D x-ray image. A confidence level is formed for the grayscale value from a first number of the available x-ray images in relation to a second number of required x-ray images for a complete reconstruction of the respective grayscale value of the 2D/3D x-ray image to be imaged.

18 Claims, 2 Drawing Sheets

(51) Int. Cl.
  *G06K 9/46*     (2006.01)
  *G06T 7/20*     (2017.01)
  *G06T 15/00*    (2011.01)
  *G06T 19/00*    (2011.01)
  *A61B 6/00*     (2006.01)
  *G06T 11/00*    (2006.01)

(52) U.S. Cl.
  CPC ... *A61B 6/5205* (2013.01); *G06T 2207/10116* (2013.01); *G06T 2211/436* (2013.01)

(56) References Cited

U.S. PATENT DOCUMENTS

| | | |
|---|---|---|
| 2007/0058772 A1 | 3/2007 | Schutz |
| 2010/0286928 A1 | 11/2010 | Dennerlein et al. |
| 2015/0173694 A1* | 6/2015 | Teshigawara .......... A61B 6/032 378/5 |

FOREIGN PATENT DOCUMENTS

| | | |
|---|---|---|
| DE | 102010034917 A1 | 2/2012 |
| DE | 102012207910 A1 | 11/2013 |
| DE | 102012217613 A1 | 3/2014 |

OTHER PUBLICATIONS

Machine translation of DE 10 2010 034 917.*
German Office Action for related German Application No. 10 2014 218 893.8, mailed Jan. 26, 2015, with English Translation.

* cited by examiner

DEVICE AND METHOD FOR ASSESSING X-RAY IMAGES

CROSS-REFERENCE TO RELATED APPLICATIONS

The present patent document claims the benefit of DE 102014218893.8, filed on Sep. 19, 2014, which is hereby incorporated by reference.

TECHNICAL FIELD

The present embodiments pertain to the field of imaging.

BACKGROUND

By way of example, three-dimensional object acquisition finds widespread use in medical engineering. Using the produced two-dimensional (2D) x-ray recordings, it is possible to generate a three-dimensional (3D) data field and, depending on the problem, reconstruct arbitrary views of an object in order to contribute to planning and/or performing surgical and/or therapeutic measures. For example, 3D data may be made from a plurality of x-ray recordings during a circular arc shaped trajectory about any object or a patient (e.g., during cone beam computed tomography). The scanned region during x-ray image acquisition may be restricted due to external conditions (e.g., caused by a possible collision with the patient or an instrument unit). These restrictions may result in incomplete scanning of the examination object and, resulting therefrom, a reduced spatial resolution and/or contrast resolution in the reconstructed 2D/3D x-ray images depending on the viewing direction onto the examination object. For example, this reduced spatial resolution and contrast resolution may lead to structures only being hinted at in a reconstructed 2D/3D x-ray image. Previously, in the case of a restricted scanned region during x-ray image acquisitions, the radiologist or medical practitioner may only make general statements (e.g., of the type that a reduction in the resolution may occur at a specific viewing angle in the case of a 2D/3D x-ray image reconstruction to be generated).

SUMMARY AND DESCRIPTION

The present embodiments relate to a method and a device for assessing reconstructed 2D/3D x-ray images based on a data matrix representing an examination object, for example a 3D data field, which is formed from a plurality of x-ray recordings. The one or more of the present embodiments assess the influence of a restricted scanned region on the imaging accuracy of a reconstructed x-ray image with respect to an object that was x-rayed.

In an embodiment, at least one device and an associated method of assessing 2D/3D x-ray images that are at least reconstructable from a 3D data field formed from a plurality of x-ray recordings includes a second module SB2 for establishing imaging accuracy. In the second module SB2, a first number of the x-ray beams that passed through an image point or this image element are summed for at least the image point of the reconstructed 2D/3D x-ray image, taking into account possible data redundancies of the individual x-ray recordings that were made along a trajectory. In a normalization unit NE, the imaging accuracy (also referred to as confidence level k) is established for an image point r(x, y, z) of a reconstructed 2D/3D x-ray image as a quotient of the first number divided by a second number required for complete imaging of an image point r(x, y, z).

According to some embodiments, provision is made for a device and a method for establishing a quality of a reconstructed x-ray image as a function of the scanned region.

One or more of the present embodiments are formed by a device and a method for providing quality information in the form of imaging accuracy or in the specification of a confidence level for image elements in reconstructed 2D/3D x-ray images.

The device and the method may include an electronic computing apparatus RE configured to receive a plurality of x-ray recordings showing an examination object from different directions, from which a 2D or 3D data field representing the examination object is generated. The computing apparatus RE is configured to establish one confidence level for a plurality of elements of the 2D/3D data field The confidence level specifies a reliability or an imaging accuracy of an imaged part of the reconstructed x-ray image from a plurality of x-ray recordings.

Data available in discretized form in Cartesian coordinates may be referred to as voxels. A value assigned to an xyz-coordinate of the data record is ascribed to a voxel. Accordingly, a voxel defines a grid point, an image point or a data element in a three-dimensional grid. A meaningful data record consisting of voxels is available if each voxel, as measured to the isocenter of the recording x-ray system, is acquired over at least a circular segment of 180 degrees plus 2 times half of the respective fan angle of the x-ray source of the x-ray system. The x-ray recordings are taken at intervals of approximately 1° or 2°, or there is at least one x-ray recording in an angle range of 1° to 2°. In practice, the scanned region is approximately a circular segment of 200° through which x-ray recordings of the object are made from the x-ray source in order to provide a 3D data field that is sufficient for reconstructing a 2D/3D x-ray image. As a result of restricting the scanned region, it is no longer the case that all required data is available for a region to be reconstructed (e.g., information for a complete 2D/3D reconstruction with respect to the reconstruction or formation of a 2D/3D x-ray image is missing for some of the voxels). In one or more embodiments, one item of quality information, in the form of imaging accuracy or a confidence level, is established for the voxels in the observation region. This respective confidence level is visualizable either directly or in a separate image for the user of the reconstructed x-ray images.

The present embodiments may provide the advantage that the user may immediately estimate the quality of a 2D/3D representation based on a representation of a spatially dependent confidence level or the user may assess whether a resolution of the reconstructed 2D/3D x-ray image is present (e.g., required for a diagnosis).

The present embodiments may provide the advantage that the user may obtain information related to how reliable the imaged structures of the reconstructed 2D/3D x-ray image are, or related to which partial volumes of an observed examination region are imaged exactly (e.g., even in the case of a restricted angle range).

The present embodiments may provide the advantage that confidence levels for image points of a reconstructed 2D/3D x-ray image may be visualizable.

The present embodiments may provide the advantage that the confidence level or levels may be superposed in the visualization of the reconstruction result and/or visualizable in a separate image.

The present embodiments may provide the advantage that spatially resolved information (e.g., a confidence level) about the influence of a restricted scanned region on the reconstruction of 2D/3D x-ray image data may be visualizable for a user (e.g., superposed over said 2D/3D x-ray image data).

DETAILED DESCRIPTION

In a device and an associated method, a statement related to an image point or an image region in a reconstructed x-ray image may be visualized in relation to the reliability of the reconstructed grayscale value for the image points of the 2D/3D x-ray image. In each case, a confidence level is formed for the grayscale value from the number of x-ray recordings made in relation to the number of x-ray recordings required for a complete reconstruction of the 2D/3D x-ray image.

According to an embodiment for assessing reconstructed 2D/3D x-ray images from a 3D data field formed from a plurality of x-ray recordings recorded of an object from different predeterminable directions, provision is made for a second module SB2 for establishing a confidence level k for an image point r(x, y, z) of a reconstructed 2D/3D x-ray image. The dividend of the confidence level k for an image point r(x, y, z) of a reconstructed 2D/3D x-ray image emerges from a first number of x-ray recordings made of an object in different angle ranges. This first number is divided by a second number of x-ray recordings of the object (O) for complete imaging of an image point r(x, y, z) in a 2D/3D x-ray image to be reconstructed. Using the second module SB2, the first number of x-ray images to be counted as part of the confidence level is determined, that emerge from the number of emerging angles, which emerge in the individual x-ray recordings between a vector v=a_i−r starting from the initial point a_i of the x-ray source in the direction of the image point r(x, y, z) and a reference plane or reference line x, y, z lying in the reconstructed x-ray image. The second module SB2 is embodied in such a way that the established angles, under which the x-ray recording of an object O during a current scan is implemented, are rounded to an angle degree and stored in a histogram. The abscissa of the histogram is subdivided to value ranges of angles between 0° and 180° in 1° increments, with the value of 1, and all histogram classes or bins with entries greater than 1 are set to 1. The confidence level k emerges from the first number, formed from the sum of the entries of all histogram bins, divided by the second number, formed from the number of x-ray recordings required for complete reconstruction of the 2D/3D x-ray image.

Figure 1:
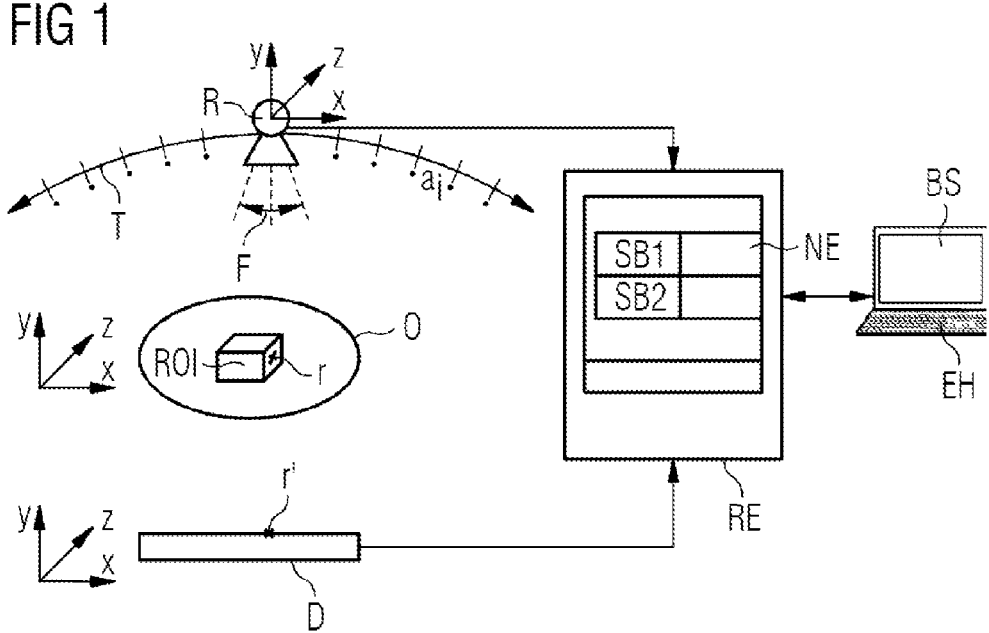
FIG. 1 depicts an example schematic illustration of an x-ray system with an associated computing unit.

FIG. 1 depicts a schematic illustration of an x-ray unit, formed by a detector D and an x-ray source R, and a computing unit RE that, inter alia, is embodied to buffer store and/or store a multiplicity of x-ray recordings, to reconstruct 2D/3D x-ray images and to establish an imaging accuracy or a confidence level relating to voxels, for example. In order to establish the confidence level, the computer has available the location of the voxels within a voxel grid in the region of interest ROI, and the geometry of the x-ray system, of the fan angle of the x-ray source R, of the spatial points of the x-ray source R on the trajectory T, and of the alignment of the detector D at the respective time of an x-ray recording. As depicted, the x-ray source R is displaceable on an arbitrary trajectory T about the object O (e.g., in this case the region of interest ROI). X-ray recordings are taken at an interval of approximately 1° on the trajectory. The position data of the x-ray source and the image data of the 2D x-ray recording are transmitted to the computing unit RE or buffer stored for further processing. On the screen BS, it is then possible to display (e.g., in an overview image) both the recorded 2D x-ray recordings and the 2D/3D x-ray images reconstructed therefrom in conjunction with the confidence level of the respective 2D/3D x-ray image either individually and/or partly or wholly superposed. By the input unit EH of the computing unit RE, it is possible to determine or verify both the trajectory T of the x-ray source R and the region of interest ROI within the object O. In a first module SB1, the imaging accuracy is calculated at least for one field of view. In the second module SB2, the imaging accuracy is calculated for determining the scanning reliability for a spatial point within a scanning plane. The mean and/or minimum confidence level is also determined in the first module SB1 from the image elements of a slice image obtained by tomography.

In an embodiment, an imaging accuracy or a confidence level $k(\underline{x})$ is calculated for each voxel $\underline{x}$ in the reconstruction volume for the purposes of a 2D/3D reconstruction of an x-ray image. The confidence level $k(\underline{x})$ reproduces the reliability of the reconstructed grayscale values $f(\underline{x})$ from the image data stored in the 3D data field. A confidence level of 1 specifies a 100% exact reconstruction and a confidence level less than 1 specifies a reduced quality of the reconstructed 2D/3D x-ray image. The confidence levels $k(\underline{x})$ are either calculated during the reconstruction and buffer storage (e.g., for further purposes as specified below), or the confidence levels are determined at the time during the volume visualization. By way of example, the confidence levels $k(\underline{x})$ may be visualized as depicted in FIG. 2 or 3.

For example, the confidence level k correlates with the number of direction contributions that contribute to the reconstruction in a voxel $\underline{x}$. If contributions from all projection directions from an angle range of at least 180 degrees plus two times half the fan angle F of the x-ray source R are present for the individual voxels $\underline{x}$, there is a complete scan of the object or of the region of interest ROI for this voxel $\underline{x}$ and the confidence level k is 100%. As described in this example, the angle range of 180 degrees is sufficient. The otherwise conventional addition plus two times the fan angle only means that the condition is valid for all voxels within the 3D field of view (FOV). Scanning is performed at an interval of approximately 1° (e.g., the x-ray source makes, in the angle range of 1°, an x-ray recording of the object O in each case). The value of the confidence level k is reduced for a voxel $\underline{x}$ that has not obtained reconstruction contributions from a sufficient number of directions. The angle range of the missing reconstruction contribution provides additional information about which edge directions in the neighborhood of the voxel $\underline{x}$ that may only be reproduced to a limited extent.

To display the reconstruction result within the scope of volume rendering, it is possible to determine a projection of the confidence level k(x) from the identical perspective in addition to the 3D view of the reconstructed volume f(x), calculated according to the conventional methods. In this visualization type, the confidence level k(x) may be superposed as a grayscale or color-coded overlay onto the image of the reconstructed 2D/3D x-ray image or volume, as depicted in FIGS. 2 and 3. This grayscale or color-coded overlay is calculated separately for each direction of view from which the volume is observed.

Figure 2:
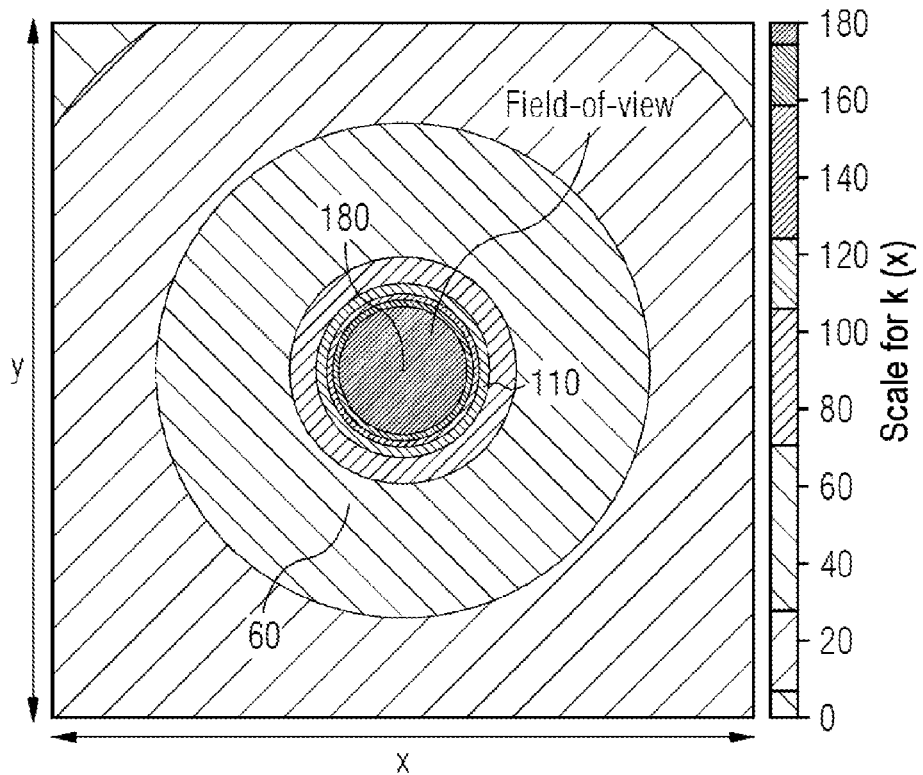
FIG. 2 depicts a distribution of the confidence level on an observation surface (x, y, 0) in the case of a circular arc-shaped scan of 200° about an object, according to one embodiment.
Figure 3:
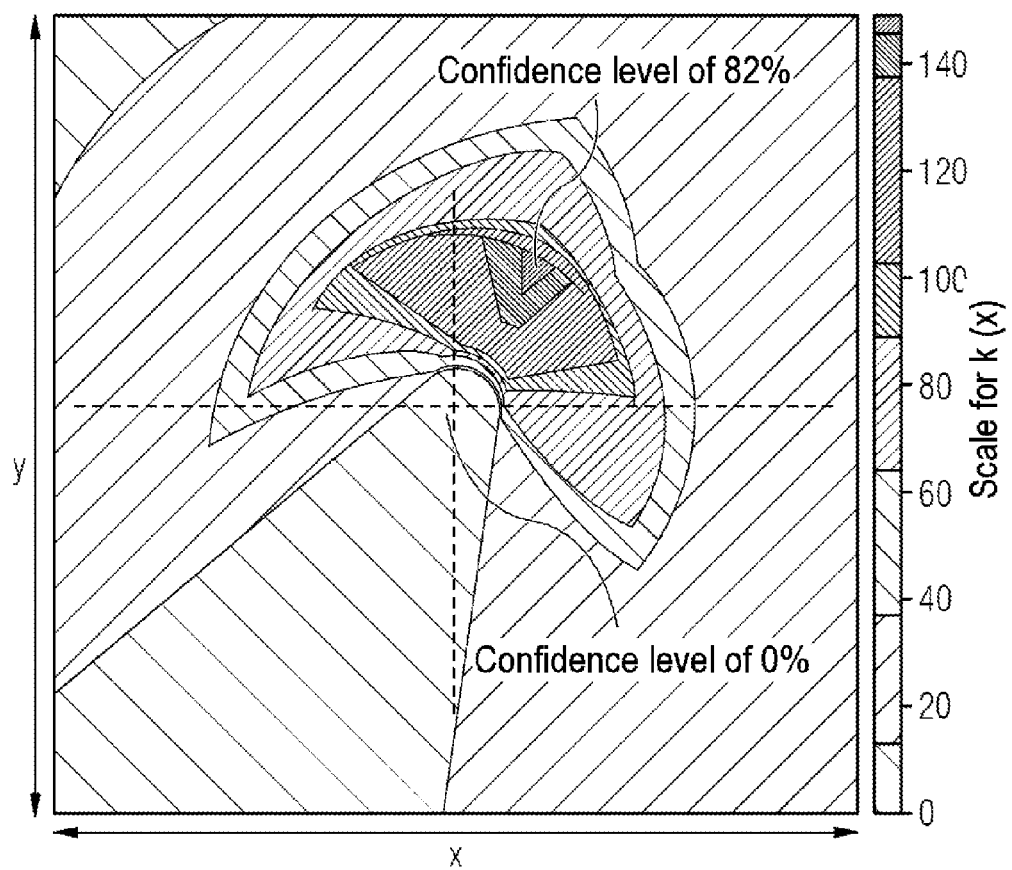
FIG. 3 depicts a distribution of the confidence level in the case of a representation on an observation surface (x, y, 0) for a scan of an ROI with a non-isocentric C-arm, according to another embodiment.

As depicted in FIG. 2, the confidence level k(x) is produced from the volume regions and imaged above a threshold T. A scale with grayscale or color values is imaged on the edge of FIGS. 2 and 3.

In selective volume rendering, two volumetric views of the reconstruction volume may be calculated for each direction of view, including: using one representation/view, producing volume regions with the confidence level above a fixed threshold T; and using a further representation/view, it is possible to display the remaining volume regions (e.g., regions that have a confidence level less than or equal to the fixed confidence level).

In a representation of individual slice images obtained by tomography from the reconstruction volume, the quality, in relation to the currently selected layer, may be reproduced in a multiplanar view. The quality is calculated as mean or minimum confidence level k(x) of all voxels in the layer. If this confidence level k(x) drops below a fixable threshold T, the multiplanar view-representation is provided with a warning, or the selection and/or view of the layer is not permitted. Therefore, the display of badly affected slice images may not permitted.

As a result of the grayscale or color-coded confidence levels k, the observer of the reconstructed x-ray image identifies the volume regions in the reconstructed 3D volume that may be excluded for a medical diagnosis or that may be used with reservations, for example. Only the volume regions with complete scanning reproduce the correct structure of the structures of the tissue established in the reconstruction. In accordance with the displayed confidence levels k(x), the radiologist or medical practitioner may obtain an overview of the region to be examined, thus producing an improved diagnosis.

The calculation of the confidence level k(x)=k(x, y) for a conventional C-arm acquisition with planar arc scanning at an interval of one degree within a plane z=0 emerges as follows.

An arbitrary point (x, y, 0) of the reconstruction volume within the orbital plane is selected.

Thereupon, all x-ray beams (e.g., straight lines of a half-domain which emanate from the x-ray source R and along which x-ray photons are emitted) that pass through this point (x, y, 0) during the recording process are considered.

The angles between these measurement beams and the X-axis are determined, with these angles being mapped to values between 0 degrees and 180 plus x degrees.

The angles from 0 to 180 degrees are plotted in a histogram that is individual to each point (x, y, 0). The abscissa of the histogram is subdivided into classes that may be referred to as bins. A bin has a width of 1 or 2 degrees. The ratio of the non-zero histogram entries to all histogram entries defines the confidence level k in the respective volume positions, determinable by the selected coordinates x and y.

In principle, the totality of all straight lines that extend through a specific voxel v and through all x-ray source points at the time of an x-ray recording along the orbit, within an angle interval or angle region of 180 degrees, are acquired.

The trajectory T of the x-ray source R is situated at the spatial point a=(ax, ay, 0) during the x-ray image acquisition. This is a planar scanning path within the az=0 plane. The spatial points in the x-ray field of view are denoted by r=(rx, ry, rz).

In a first module SB1 arranged in the computing unit RE, the scanning reliability is established by a first algorithm for calculating scanning reliability for a "region of interest" (ROI) or "field of view" (FOV), and possibly for regions which extend therebeyond.

Act 1 includes setting a multiplicity of nodes r_i for spatial points within the scanning plane.

Act 2 includes calculating the scanning reliability for these nodes using a second algorithm stored in the second module SB2.

Act 3 includes interpolating the scanning reliability values for all spatial points r within the scanning plane for rz=0 from the values of the nodes determined in act 2.

Act 4 includes extrapolating the scanning reliability values for spatial points outside of the scanning plane by the following prescription: the scanning reliability for k=(rx, ry, rz) is identical to the scanning reliability for r=(rx, ry, 0). The values determined in act 3 for the scanning plane are likewise considered valid for all spatial planes parallel to the scanning plane. This assumption is valid for relatively small cone values.

The scanning reliability for a spatial point r=(rx, ry, 0) within the scanning plane is determinable by the second calculation prescription stored in the second module SB2.

Act 0 includes initializing a histogram data structure with 180 bins (HIST[0 . . . 179]) with a value 0 for each bin.

Act 1 includes passing through all points of the x-ray source on the trajectory a_i at which projection data are acquired. Act 1 may include the optional act of performing an interpolation in order to produce intermediate points if the scanning density of the points a_i is too low. For each of these points, optional sub-acts 1A-1E may be performed.

Act 1A includes determining whether the point r was projected onto the active detector surface during the x-ray projection at a_i. Proceed with act 1B only in the affirmative.

Act 1B includes generating the vector v=a_i−r.

Act 1C includes calculating the angle w between the vector v determined in act 1A and the x-axis by inverse trigonometric functions.

Act 1D includes rounding the angle w to an angle degree.

Act 1E includes incrementing the histogram value HIST [w] by 1.

Act 2 includes setting all histogram bins with entries >1 to 1.

Act 3 includes summing the entries of all histogram bins.

The dividend (e.g., the number value which was described as "first number" in the description) is available after act 3. In act 4, the divisor (e.g., described as "second number" in the description) is specified to be 180.

Act 4 includes dividing the sum value by 180.

The result of act 4 provides the confidence level k(x) for the spatial point r.

By way of example, FIG. 2 depicts a distribution of the confidence level k(x) on an observation surface (x, y, 0) in the case of a circular arc-shaped scan of 220°.

FIG. 3 depicts a distribution of the confidence level k(x) when displayed on an observation surface (x, y, 0) for scanning an ROI using a non-isocentric C-arm.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for assessing reconstructed x-ray images from a three-dimensional (3D) data field formed from a plurality of x-ray images recorded of an object from different predeterminable directions in different angle ranges along a trajectory, the apparatus comprising:
   an x-ray system configured to establish a confidence level for an image point of a reconstructed x-ray image,
   wherein the different angles are rounded to an angle degree and stored in a histogram bin for the corresponding angle degree with a value of 1,
   wherein an abscissa of the histogram is subdivided into value ranges between 0 and 180 degrees in 1 degree increments,
   wherein all histogram bins with entries greater than 1 are set to 1,
   wherein the confidence level emerges from a first number of the x-ray images of the object formed from a sum of the entries of all histogram bins divided by a second number of the x-ray images of the object required for complete reconstruction of the reconstructed x-ray image.

2. The apparatus of claim 1, wherein the first number of x-ray images are recorded from the number of different angles, and
   wherein the first number of x-ray images emerge in individual x-ray images between a vector formed from the initial point of the x-ray source in a direction of the image point and a reference plane or reference line lying in the reconstructed x-ray image along a trajectory around the object.

3. The apparatus of claim 2, wherein the X-ray system is further configured to establish a mean confidence level, a minimum confidence level, or both the mean confidence level and the minimum confidence level from image elements of a slice image obtained by tomography.

4. The apparatus of claim 3, wherein volume regions: (1) are produced for a representation when the confidence levels lie above a fixable threshold; (2) are representable in a further representation when the confidence levels are less than or equal to the fixed threshold; or (3) are produced for a representation when the confidence levels lie above the fixable threshold and are representable in the further representation when the confidence levels are less than or equal to the fixed threshold.

5. The apparatus of claim 4, wherein the image point is a voxel.

6. The apparatus of claim 1, wherein the X-ray system is further configured to establish a mean confidence level, a minimum confidence level, or both the mean confidence level and the minimum confidence level from image elements of a slice image obtained by tomography.

7. The apparatus of claim 6, wherein volume regions: (1) are produced for a representation when the confidence levels lie above a fixable threshold; (2) are representable in a further representation when the confidence levels are less than or equal to the fixed threshold; or (3) are produced for a representation when the confidence levels lie above the fixable threshold and are representable in the further representation when the confidence levels are less than or equal to the fixed threshold.

8. The apparatus of claim 7, wherein the image point is a voxel.

9. The apparatus of claim 1, wherein volume regions: (1) are produced for a representation when the confidence levels lie above a fixable threshold; (2) are representable in a further representation when the confidence levels are less than or equal to the fixed threshold; or (3) are produced for a representation when the confidence levels lie above the fixable threshold and are representable in the further representation when the confidence levels are less than or equal to the fixed threshold.

10. The apparatus of claim 9, wherein the image point is a voxel.

11. The apparatus of claim 1, wherein the image point is a voxel.

12. A method for assessing reconstructed x-ray images from a three-dimensional (3D) data field formed from a plurality of x-ray images recorded of an object from different predeterminable directions, the method comprising:
   establishing a confidence level for an image point of a reconstructed x-ray image from a first number of the x-ray images of the object in different angle ranges as seen along a trajectory divided by a second number of the x-ray images of the object for complete imaging of an image point in the reconstructed x-ray image, wherein the different angles are rounded to an angle degree and stored in a histogram bin for the corresponding angle degree with a value of 1, wherein an abscissa of the histogram is subdivided into value ranges between 0 and 180 degrees in 1 degree increments, wherein all histogram bins with entries greater than 1 are set to 1, and wherein the confidence level emerges from the first number formed from the sum of the entries of all histogram bins divided by the second number formed from the number of x-ray images required for complete reconstruction of the reconstructed x-ray image; and
   visualizing the confidence level.

13. The method of claim 12, wherein the first number of x-ray images are recorded from the number of different angles, and
   wherein the first number of x-ray images emerge in individual x-ray recordings between a vector formed from the initial point of the x-ray source in the direction of the image point and a reference plane or reference line lying in the reconstructed x-ray image along a trajectory around the object.

14. The method of claim 13, further comprising:
   establishing a mean confidence level, a minimum confidence level, or both the mean confidence level and the minimum confidence level from image elements of a slice image obtained from tomography.

15. The method of claim 14, further comprising:
   (1) producing volume regions for a representation when the confidence levels are above a fixable threshold;

(2) establishing volume regions in a representation when the confidence levels are less than or equal to the fixed threshold; or (3) producing volume regions for a representation when the confidence levels are above the fixable threshold and establishing the remaining volume regions in a further representation when the confidence levels are less than or equal to the fixed threshold.

16. The method of claim 12, further comprising:

establishing a mean confidence level, a minimum confidence level, or both the mean confidence level and the minimum confidence level from image elements of a slice image obtained from tomography.

17. The method of claim 16, further comprising:

producing volume regions for a representation when the confidence levels are above a fixable threshold;

establishing the remaining volume regions in a further representation when the confidence levels are less than or equal to the fixed threshold; or producing volume regions for a representation when the confidence levels are above the fixable threshold and establishing the remaining volume regions in the further representation when the confidence levels are less than or equal to the fixed threshold.

18. The method of claim 12, further comprising:

(1) producing volume regions for a representation when the confidence levels are above a fixable threshold;

(2) establishing volume regions in a representation when the confidence levels are less than or equal to the fixed threshold; or (3) producing volume regions for a representation when the confidence levels are above the fixable threshold and establishing the remaining volume regions in a further representation when the confidence levels are less than or equal to the fixed threshold.

* * * * *